United States Patent [19]
Conrad

[11] 3,931,233
[45] Jan. 6, 1976

[54] PROCESS FOR THE PRODUCTION OF 5-BROMO-5-NITRO-1,3-DIOXANE

[75] Inventor: Jens Conrad, Hilden, Germany

[73] Assignee: Henkel & Cie G.m.b.H., Dusseldorf, Germany

[22] Filed: Sept. 13, 1973

[21] Appl. No.: 396,885

[30] Foreign Application Priority Data
Dec. 23, 1972 Germany............................ 2263206

[52] U.S. Cl. ............................................. 260/340.7
[51] Int. Cl.² ...................................... C07D 319/06
[58] Field of Search ................................ 260/340.7

[56] References Cited
FOREIGN PATENTS OR APPLICATIONS
1,507,444  11/1967  France ............................ 260/340.7

Primary Examiner—Norma S. Milestone
Attorney, Agent, or Firm—Hammond & Littell

[57] ABSTRACT

An improved process for the production of 5-bromo-5-nitro-1,3-dioxane by the acetalization of formaldehyde with 2-bromo-2-nitro-propanediol-1,3 in the presence of concentrated sulfuric acid as a catalyst and recovery of readily crystallizable 5-bromo-5-nitro-1,3-dioxane.

6 Claims, No Drawings

PROCESS FOR THE PRODUCTION OF 5-BROMO-5-NITRO-1,3-DIOXANE

THE PRIOR ART

In copending, commonly-assigned U.S. Pat. application Ser. No. 190,827, filed Oct. 20, 1971, now U.S. Pat. No. 3,772,443 (a division of Ser. No. 29,692, filed Apr. 17, 1970, now abandoned), the method of use of 5-bromo-5-nitro-1,3-dioxane in anti-microbial compositions is described. In this application, the production of 5-bromo-5-nitro-1,3-dioxane is shown by acetalization of formaldehyde with 2-bromo-2-nitro-propanediol-1,3 in the presence of p-toluenesulfonic acid and preferably polyphosphoric acid as acid catalysts. The technical performance of these syntheses is made extremely difficult by the fact that the product produced, 5-bromo-5-nitro-1,3-dioxane, is very impure and cannot be purified by a simple method. The purification is performed according to this application by means of the costly processes of vapor distillation and sublimation under a high vacuum or by steam distillation. There is a great interest, therefore, in a process which permits the manufacture of a pure product at much less cost.

In addition, Eckstein et al, Chemical Abstracts, 49, 10299d (1955), describes a process for the preparation of derivatives of 5-bromo-5-nitro-1,3-dioxane by the reaction of 2-bromo-2-nitro-propanediol-1,3 with the corresponding aldehyde where 0.1 gm of benzenesulfonic acid and 200 ml of anhydrous benzene were employed per mol of diol. The mixture was azeotropically distilled until cessation of water evolution and thereafter one drop of sulfuric acid was added and the reaction continued to cessation of water evolution, for a total reaction of 6 to 8 hours. After distilling off the benzene, the acetal was extracted by anhydrous ethanol and crystallized. This process requires lengthy time and elaborate recovery methods.

OBJECTS OF THE INVENTION

An object of the present invention is the development of an improved method for the production of 5-bromo-5-nitro-1,3-dioxane which does not require costly methods of purification.

Another object of the present invention is the development of a process for the production of 5-bromo-5-nitro-1,3-dioxane consisting essentially of condensing formaldehyde with 2-bromo-2-nitro-propanediol-1,3 in the presence of an inert water-immiscible organic solvent and concentrated sulfuric acid as sole catalyst at temperatures between 40°C and 110°C under conditions whereby water produced is removed from the reaction, and recovering said 5-bromo-5-nitro-1,3-dioxane.

These and other objects of the present invention will become more apparent as the description thereof proceeds.

DESCRIPTION OF THE INVENTION

In further developing the process for the production of 5-bromo-5-nitro-1,3-dioxane, it was now found that concentrated sulfuric acid can advantageously be used as an acid catalyst.

In carrying out the synthesis by the process according to the invention using concentrated sulfuric acid as catalyst in a two-phase system, it appears that the difficulties which existed when using p-toluenesulfonic acid and polyphosphoric acid did not occur and that a pure product was obtained with high yield without the need of a complicated purification. This result of the process of the invention was surprising and by no means predictable, since in other acetalizations with sulfuric acid as catalyst, resinifications very often occurred. Apparently this was why, in one instance, the prior art suggested use of benzenesulfonic acid first and then finishing the reaction with sulfuric acid.

The present invention therefore is directed to a process for the production of 5-bromo-5-nitro-1,3-dioxane consisting essentially of condensing formaldehyde with 2-bromo-2-nitro-propanediol-1,3 in the presence of an inert water-immiscible organic solvent and concentrated sulfuric acid as sole catalyst at temperatures between 40°C and 110°C under conditions whereby water produced is removed from the reaction, and recovering said 5-bromo-5-nitro-1,3-dioxane.

5-Bromo-5-nitro-1,3-dioxane is readily prepared by reacting 2-bromo-2-nitro-propanediol-1,3 with formaldehyde or a material which forms formaldehyde under the reaction conditions, such as paraformaldehyde in the presence of the concentrated sulfuric acid catalyst and recovering the desired compound. Preferably the reaction is conducted under substantially anhydrous conditions and the water produced by the reaction is either removed by azeotropic distillation or absorbed by an excess of concentrated sulfuric acid. The reactants are employed in substantially equimolar amounts. However, a small excess of either reactant may be employed. A preferred ratio of reactants is 1.01 to 1.5 mols of 2-bromo-2-nitro-propanediol-1,3 to 1 mol of formaldehyde. If the formaldehyde is introduced as paraformaldehyde, it is charged in an amount equivalent to its formaldehyde content. The reaction is conducted at elevated temperatures of from 40°C to 110°C, preferably at the reflux temperature, and in the presence of anhydrous water-immiscible organic solvents, preferably one from which water may be azeotropically distilled.

To carry out the process of the invention, 2-bromo-2-nitro-propanediol-1,3 and paraformaldehyde in the calculated quantities were dissolved in an inert solvent, preferably ethylene chloride. Concentrated sulfuric acid was added in drops to the boiling, vigorously stirred solution. If one operates with catalytic quantities of acid, such as from 0.01 percent to 5 percent by weight, based on the weight of the reactants, the water formed in the reaction must be removed, preferably by azeotropic distillation. However, if an amount of sulfuric acid sufficient to bind the water of reaction is used, such as an amount which, when fully diluted by the water formed, is at least 35 percent by weight sulfuric acid, it suffices to agitate the two-phase mixture for two hours with reflux at elevated temperature. Preferably the inert water-immiscible organic solvent is one which boils between 40°C and 110°C, preferably between 60°C and 90°C.

The working up of the reaction mixture is very simple in both procedures. After the mixture has cooled, the sulfuric acid separated as the lower phase is removed and the organic phase is washed several times with water. After evaporation of the ethylene chloride, there remains as residue practically pure, promptly crystallizing 5-bromo-5-nitro-1,3-dioxane in almost quantitative yield. To obtain a high purity product, the crude product, which is obtained in a yield of 97% to 98% of theory, can be recrystallized, for example, from aqueous methanol with little loss. The product thus obtained is gas-chromatographically pure, stable in storage and odor stable, and melts at 59°C to 61°C.

Neither the 5-bromo-5-nitro-1,3-dioxane produced according to the prior art by condensation of 2-bromo-2-nitro-propanediol-1,3 with paraformaldehyde by means of polyphosphoric acid, nor that produced by means of p-toluenesulfonic acid and azeotropic removal of the water of reaction, could be purified thus simply. The product produced by means of polyphosphoric acid and recrystallized from aqueous methanol had a fatty appearance, a smeary feel and was not pourable. Due to impurities, a strongly pungent odor developed after a short storage time.

The 5-bromo-5-nitro-1,3-dioxane produced by means of p-toluenesulfonic acid in catalytic amounts with azeotropic removal of the water of reaction by means of benzene was obtained as an oil and could not be made to crystallize either by itself or from aqueous methanol. To get a useful product, purification by steam distillation was required.

The following examples will explain the subject of the present invention in greater detail, without limiting it thereto, however.

EXAMPLE 1

100 gm (0.5 mol) of 2-bromo-2-nitro-propanediol-1,3 were dissolved with agitation in 250 ml of ethylene chloride at the boiling temperature. After the addition of 18 gm (0.6 mol) of paraformaldehyde, stirring was continued for a short time. Then 0.5 ml of concentrated sulfuric acid was added to the boiling mixture and azeotropic distillation with separation of water was continued for three hours. The solution, cooled to room temperature, was washed three times with 100 ml of water, filtered, and the solvent was evaporated under vacuum. The resulting faintly yellow oil soon solidified as an almost colorless, crystalline mass of 5-bromo-5-nitro-1,3-dioxane.

Yield: 102.5 gm (97 percent)
Melting point: 57°C to 60°C

For larger batches, containing greater amounts of concentrated sulfuric acid, it is advisable to separate the sulfuric acid phase before washing the organic phase.

EXAMPLE 2

1200 gm (6 mols) of 2-bromo-2-nitro-propanediol-1,3 and 186 gm (6.2 mols) of paraformaldehyde in 3 liters of boiling ethylene chloride were slowly mixed with 240 ml of concentrated sulfuric acid while stirring. The agitation was continued for two hours at boiling temperature. The mixture was then cooled to room temperature and the sulfuric acid was separated. The pale yellow organic phase was washed four times with 1 liter of water. The oil remaining upon evaporation of the solvent under vacuum solidified upon cooling in coarse, almost colorless crystals of 5-bromo-5-nitro-1,3-dioxane.

Yield: 1245 gm (98 percent)
Melting point: 57°C to 60°C

One part by weight of the 5-bromo-5-nitro-1,3-dioxane obtained was recrystallized from 1 to 1.5 parts by volume of methanol/water (80:20). The product, dried under vacuum over calcium chloride or in a thin layer in air, melted at 59° to 61°C, was pourable gas-chromatographically pure, and stable on storage and odor stable.

An advantage of the process according to the invention is that it permits the production of much purer products by simple means compared with the process of the prior art. In addition, the process of the invention gives considerably better yields compared with the production method by means of p-toluenesulfonic acid. As a further advantage of the process of the invention, it may be stated that the sulfuric acid used in the synthesis can be separated virtually completely after the reaction. Thus only traces of sulfuric acid get into the effluent water with the wash water, which in view of sewage purification and protection of the environment must be regarded as an advantage not to be underestimated.

The product, a cyclic acetal of 2-bromo-2-nitro-propanediol-1,3, has been found to possess an excellent activity against bacteria and fungi in very low concentrations. The new compound is stable in the alkaline region and also is only decomposed by strong acids when hot, into 2-bromo-2-nitro-propanediol-1,3 and formaldehyde which two likewise are very active antimicrobial substances.

The advantage obtainable with the substance according to the invention consists in that, owing to its great activity and good stability, it is possible to prepare with it neutral, acid and also alkaline compositions which ensure a positive protection against bacterial and fungal attack.

The preceding specific embodiments are illustrative of the practice of the invention. It is to be understood, however, that other expedients known to those skilled in the art may be employed without departing from the spirit of the invention or the scope of the appended claims.

I claim:

1. A process for the production of 5-bromo-5-nitro-1-3-dioxane consisting essentially of condensing the reactants formaldehyde and 2-bromo-2-nitro-propanediol-1,3, in substantially equimilar amounts in the presence of the inert water-immiscible organic solvent ethylene chloride, and concentrated sulfuric acid as sole catalyst under conditions whereby water produced is removed from the reaction, said concentrated sulfuric acid being slowly added to said solution of reactants at the reflux temperature and recovering said 5-bromo-5-nitro-1,3-dioxane.

2. The process of claim 1, wherein there is from 1.01 to 1.5 mols of 2-bromo-2-nitro-propanediol-1,3 per 1 mol of formaldehyde.

3. The process of claim 1, wherein said water produced is removed by azeotropic distillation.

4. The process of claim 3 wherein there is from 0.01 to 5 percent by weight, based upon the weight of said reactants, of said sulfuric acid present as said sole catalyst.

5. The process of claim 1 wherein said water produced is removed from the reaction by an excess of concentrated sulfuric acid.

6. The process of claim 5 wherein said excess of concentrated sulfuric acid used is an amount, which when fully diluted by the water produced, is at least 35 percent by weight sulfuric acid.

* * * * *